United States Patent [19]
White, Jr.

[11] 4,181,799
[45] Jan. 1, 1980

[54] 5(6H), 8(8aH)-DIOXO-1H,3H-THIAZOLO[4,3-c]

[75] Inventor: Ralph L. White, Jr., Norwich, N.Y.
[73] Assignee: Morton-Norwich Products, Inc., Norwich, N.Y.
[21] Appl. No.: 960,078
[22] Filed: Nov. 13, 1978
[51] Int. Cl.² .................................... C07D 513/04
[52] U.S. Cl. ........................................... 544/48
[58] Field of Search .................................. 544/48

Primary Examiner—John M. Ford
Attorney, Agent, or Firm—Anthony J. Franze

[57] ABSTRACT

The compound 5(6H), 8(8aH)-dioxo-1H,3H-thiazolo[4,3-c] [1,4]thiazine is useful as an inhibitor of Angiotensin I converting enzyme.

1 Claim, No Drawings

5(6H), 8(8aH)-DIOXO-1H,3H-THIAZOLO[4,3-c] [1,4]THIAZINE

This invention is concerned with the compound 5(6H), 8(8aH)-dioxo-1H,3H-thiazolo[4,3-c] [1,4]thiazine.

This compound is a potent inhibitor of the enzyme responsible for converting the decapeptide Angiotensin I to the octapeptide Angiotensin II. Angiotensin II is the powerful pressor agent implicated as the causative agent in some forms of hypertension.

Of late, it has been recognized that a substance capable of interrupting the pathway whereby Angiotensin II is produced, viz.; the conversion hereabove referred to, presents a useful and effective means of combatting hypertension associated with that pressor agent.

It has been discovered that the compound of this invention is possessed of noteworthy activity in inhibiting Angiotensin I converting enzyme. Thus, in in vitro techniques designed to evince such activity this compound is highly effective. For example, it inhibits the pure converting enzyme isolated from rabbit lung tissue at a level of about $2.4 \times 10^{-5}$ moles per liter. It is, therefore, a notable Angiotensin I converting enzyme inhibitor.

The compound of this invention is not limited to in vitro manifestations of its converting enzyme inhibiting propensity. Upon oral administration, a dose dependent antihypertensive effect in acute aortic coarctation hypertensive rats is elicited. Such oral dosage as, for example, a suspension of 0.5% Methocel solution to achieve an $ED_{30}$ (calculated oral dosage for a reduction of 30 mm Hg in mean arterial blood pressure) is about 35 mg/kg.

The method currently preferred for the preparation of the compound of this invention is illustrated in the following description.

5(6H),8(8aH)-Dioxo-1H,3H-thiazolo[4,3-c] [1,4]thiazine (R) 3-(Mercaptoacetyl)thiazolidine-4-carboxylic acid (12.1 g, 0.058 mole), triethylamine (8.1 ml, 0.058 mole), dimethylformamide (250 ml) and diphenylphosphoryl azide (12.5 ml, 0.058 mole) were stirred for 6.0 hours, then allowed to stand under ambient conditions for 18 hours. This solution was poured into ice and $H_2O$ (~2.5 liter) and stirred for 1.5 hours. The resulting solution was extracted with $CHCl_3$ (4×450 ml), washed with $H_2O$ (3×500 ml) and dried over $MgSO_4$. The filtered extract was concentrated by vacuum distillation to an oil which solidified upon scratching. Recrystallization twice from 2-propanol gave 6.5 g (0.034 mole, 59%) of product.

The analytical sample was obtained by drying at room temperature in vacuo to give melting point 101°–103°.

Anal. Calcd. for $C_6H_7NO_2S_2$: C, 38.07; H, 3.73; N, 7.40. Found: C, 37.80; H, 3.60; N, 7.29.

What is claimed is:
1. The compound 5(6H),8(8aH)-dioxo-1H,3H-thiazolo[4,3-c] [1,4]thiazine.

* * * * *